(12) United States Patent
Brendel

(10) Patent No.: US 7,327,553 B2
(45) Date of Patent: Feb. 5, 2008

(54) FEEDTHROUGH CAPACITOR FILTER ASSEMBLIES WITH LAMINAR FLOW DELAMINATIONS FOR HELIUM LEAK DETECTION

(76) Inventor: Richard L. Brendel, 1551 Jefferson Dr., Carson City, NV (US) 89706

( * ) Notice: Subject to any disclaimer, the term of this patent is extended or adjusted under 35 U.S.C. 154(b) by 273 days.

(21) Appl. No.: 11/161,198

(22) Filed: Jul. 26, 2005

(65) Prior Publication Data

US 2006/0023397 A1    Feb. 2, 2006

Related U.S. Application Data

(60) Provisional application No. 60/591,743, filed on Jul. 27, 2004.

(51) Int. Cl.
*H01G 4/35* (2006.01)

(52) U.S. Cl. .................. 361/302; 361/303; 361/305; 361/308.1; 361/306.1; 333/182; 333/185; 607/5

(58) Field of Classification Search ........ 361/302–305, 361/308.1, 308.2; 333/182, 185; 607/5
See application file for complete search history.

(56) References Cited

U.S. PATENT DOCUMENTS

| | | | |
|---|---|---|---|
| 4,362,792 A * | 12/1982 | Bowsky et al. ............. | 429/181 |
| 4,424,551 A | 1/1984 | Stevenson et al. | |
| 5,333,095 A | 7/1994 | Stevenson et al. | |
| 5,751,539 A | 5/1998 | Stevenson et al. | |
| 5,825,608 A * | 10/1998 | Duva et al. .................. | 361/302 |
| 5,870,272 A * | 2/1999 | Seifried et al. ............. | 361/302 |
| 5,905,627 A | 5/1999 | Brendel et al. | |
| 5,973,906 A | 10/1999 | Stevenson et al. | |
| 6,008,980 A * | 12/1999 | Stevenson et al. .......... | 361/302 |
| 6,414,835 B1 * | 7/2002 | Wolf et al. .................. | 361/302 |
| 6,566,978 B2 * | 5/2003 | Stevenson et al. .......... | 333/182 |
| 6,765,779 B2 | 7/2004 | Stevenson et al. | |
| 6,888,715 B2 * | 5/2005 | Stevenson et al. .......... | 361/302 |

* cited by examiner

*Primary Examiner*—Nguyen T. Ha
(74) *Attorney, Agent, or Firm*—Kelly Lowry & Kelley LLP

(57) ABSTRACT

A feedthrough filter capacitor assembly includes a capacitor having first and second sets of conductive electrode plates embedded within a dielectric body and mounted to the hermetic terminal of an implantable medical device. A laminar delamination gap is provided between the capacitor sealing materials and the hermetic terminal assembly to facilitate helium leak detection. At least one feedthrough terminal pin extends through the capacitor in conductive relation with the first set of electrode plates, and an outer ferrule is mounted about the capacitor in conductive relation with the second set of electrode plates. The mounting washer is spaced against the hermetic seal and is adhesively connected to the feedthrough capacitor. The mounting washer forms a laminar flow delamination through which helium molecules can flow during a helium leak detection test. Provision is made for a pre-connection to the gold braze so that the capacitor inside diameter termination is not electrically isolated from the lead wire.

20 Claims, 5 Drawing Sheets

FEEDTHROUGH CAPACITOR FILTER ASSEMBLIES WITH LAMINAR FLOW DELAMINATIONS FOR HELIUM LEAK DETECTION

BACKGROUND OF THE INVENTION

This invention relates generally to feedthrough capacitor filter assemblies, particularly of the type used in implantable medical devices such as cardiac pacemakers, cardioverter defibrillators and the like, to decouple and shield internal electronic components of the medical device from undesirable electromagnetic interference (EMI) signals. More specifically, this invention relates to an improved feedthrough capacitor filter assembly of the type incorporating a hermetic seal to prevent passage or leakage of fluids through the filter assembly, wherein a laminar flow delamination is provided to accommodate and facilitate post manufacture and pre-usage testing of the hermetic seal.

Feedthrough terminal pin assemblies are generally well known in the art for use in connecting electrical signals through the housing or case of an electronic instrument. For example, in implantable medical devices such as cardiac pacemakers, defibrillators and the like, the terminal pin assembly comprises one or more conductive terminal pins supported by an insulator structure for feedthrough passage of electrical signals from the exterior to the interior of the medical device. Many different insulator structures and related mounting methods are known for use in medical devices wherein the insulator structure provides a hermetic seal to prevent entry of patient body fluids into the medical device housing, where such body fluids could otherwise interfere with the operation of and/or cause damage to internal electronic components of the medical device.

In the past, two primary technologies have been employed to manufacture the hermetic seal. One technique involves the use of an alumina insulator which is sputtered to accept brazing material. This alumina insulator is brazed to the terminal pin or pins, and also to an outer metal ferrule of titanium or the like. The alumina insulator supports the terminal pin or pins in insulated spaced relation from the ferrule which is adapted for suitable mounting within an access opening formed in the housing of the medical device. In an alternative technique, the hermetic seal comprises a glass-based seal forming a compression or fused glass seal for supporting the terminal pin or pins within an outer metal ferrule.

The feedthrough terminal pins are typically connected to one or more lead wires which, in the example of a cardiac pacemaker, sense signals from the patient's heart and also couple electronic pacing pulses from the medical device to the patient's heart. Unfortunately, these lead wires can act as an antenna to collect stray electromagnetic interference (EMI) signals for transmission via the terminal pins into the interior of the medical device. Such unwanted EMI signals can disrupt proper operation of the medical device, resulting in malfunction or failure. For example, it has been documented that stray EMI signals emanating from cellular telephones can inhibit pacemaker operation, resulting in asynchronous pacing, tracking and missed beats. To address this problem, hermetically sealed feedthrough terminal pin assemblies have been designed to include a filter capacitor for decoupling EMI signals in a manner preventing such unwanted signals from entering the housing of the implantable medical device. See, for example, U.S. Pat. Nos. 4,424,551; 5,333,095; 5,751,539; 5,905,627; 5,973,906; 6,008,980; and 6,566,978.

While feedthrough capacitor filter assemblies have provided a significant advance in the art, one potential area of concern is that the filter capacitor is often incorporated into the terminal pin assembly in a way that can mask a defective hermetic seal. More particularly, a defective braze or a defective glass-based seal structure, which would permit undesirable leakage of patient body fluids when mounted on a medical device and implanted into a patient, can be obstructed by the mounting of the filter capacitor and its associated electromechanical connections. For example, with reference to the feedthrough filter capacitor shown in U.S. Pat. No. 4,424,551, a ceramic filter capacitor is bonded to a glass seal and then embedded in epoxy material. Typical post-manufacture leak testing is performed by mounting the feedthrough assembly in a test fixture, and then subjecting one side of the feedthrough assembly to a selected pressurized gas such as helium. While the bulk permeability of the epoxy material is such that helium under pressure can penetrate therethrough in the presence of a defective hermetic seal, the duration of this pressure test (typically a few seconds) is often insufficient to permit such penetration. Accordingly, the epoxy material can mask the defective hermetic seal. The thus-tested feedthrough assembly can then mistakenly be incorporated into a medical device and implanted into a patient, wherein slow leakage of patient body fluids through the feedthrough assembly can cause the medical device to malfunction or fail.

FIGS. 1 and 2, taken from FIGS. 1 and 2 of U.S. Pat. No. 6,566,978, disclose a quadpolar feedthrough capacitor 16 mounted on a quadpolar terminal 10. A gap 38 is formed between the ceramic capacitor 16 and the alumina hermetic seal insulator 36. The purpose of this gap 38 is to allow for ready passage of leak detection gases from the hermetic terminal areas or along lead wire 14 through the insulator 36 to flow to the leak detection vent hole 39. However, providing such a gap 38 between the ceramic capacitor 16 and the insulator 36 surface can result in the tendency to trap contaminants, cleaning solvents or the like into this enclosed space. Conductive polyimides are typically used to form the electrical connection between the lead wire 14 and the inside diameter 22 of the ceramic capacitor 16. Conductive polyimides are also typically used to form the connection between the capacitor 16 outside diameter metallization 25 and the ferrule 26. After curing, these conductive polyimide materials are typically cleaned using a grit blasting system with sodium bicarbonate as the blasting medium. Sodium bicarbonate, otherwise known as baking soda, is highly soluble in water. Accordingly, de-ionized water rinses are used to ensure that no baking soda is left on the part but the sodium bicarbonate dissolves readily into the water cleaning solvent. After drying out, trace elements of the sodium bicarbonate are then left inside any cavity or air gap, for example, the gap 38 formed between the ceramic capacitor 16 and the alumina insulator 36 described in the U.S. Pat. No. 6,566,978. After drying, a sodium bicarbonate residue is very hygroscopic. That is, it will tend to absorb moisture from the surrounding air which can degrade the electrical insulation properties of the feedthrough filtered capacitor assembly 10.

For medical implant applications, it is typical that the insulation resistance requirement be 100 Gigaohms or even higher. In order to consistently achieve an insulation resistance greater than 100 Gigaohms, it is essential that all surfaces be extremely clean. Accordingly, any trace element of sodium bicarbonate or other contaminant left behind leads to rejection of the devices.

Another issue associated with gaps 38 between the ceramic capacitor 16 and the insulator 36 of the ferrule 26 mounting surface is associated with the high voltage requirements of an implantable cardioverter defibrillator. Even low voltage devices like pacemakers are sometimes subjected to high voltage pulses. This is typical during an external defibrillation event. There has been a proliferation of automatic external defibrillators (AEDs) in the marketplace. One can now find AEDs in airplanes, hotels, sporting places and many other public venues. Accordingly, pacemaker wearers are being subjected to an ever-increasing number of high voltage shocks in the patient environment. Referring to FIGS. 2, 6 and 9 of U.S. Pat. No. 6,566,978, one can see that the gap (38, 138 or 238) is an area where electric field enhancement can occur. That is, when a high voltage is applied to the lead wire 18, there could be a tendency for a high electric field stress to occur in the air gap 38. These high electric field stresses can lead to ionization of the air gap 38, a resulting plasma and a catastrophic high voltage breakdown of the device 10. This so called avalanche breakdown would cause an implantable medical device to not function, which would of course be life threatening for a pacemaker or a defibrillator dependent patient.

FIGS. 3 and 4, taken from FIGS. 5 and 6 of U.S. Pat. No. 6,765,779, disclose a unipolar feedthrough capacitor 100 mounted on a unipolar hermetic terminal 102. The feedthrough capacitor 100 incorporates outer diameter metallization 114. An electrical attachment 132 is made from the capacitor outside diameter 114 to the ferrule 118. This connection 132 is typically formed with a high temperature thermal setting conductive polymer such as a conductive polyimide. There are gaps left around the circumference of connection material 132 to provide for helium leak detection pathways. This is generally described in U.S. Pat. No. 6,765,779 in column 2 lines 24 through 67 and in column 3 lines 1 through 33. There is also an axial gap 126 formed between the ceramic feedthrough capacitor 100 and the surface of the hermetic terminal 102. The purpose of this axial gap 126 is so that if there was a defective gold braze 128, 130, helium atoms could readily penetrate the annular space between the lead wire 116 and the inside diameter of the insulator 124. Accordingly, said helium atoms could then pass readily through axial gap 126 and out through the spaces left in the circumferential conductive polyimide attachment material 132.

As previously mentioned, leaving an axial gap 126 can trap contaminants between the capacitor 100 and the insulator 124 or terminal 102 and also has the tendency to enhance (squeeze or compress) electric fields during the application of a high voltage to the device.

Accordingly, there is a need for an EMI filtered hermetic feedthrough terminal assembly suitable for human implant that will avoid the field enhancement issues associated with an air gap, but at the same time provides for a helium leak detection path. The present invention fulfills this need by providing an improved feedthrough capacitor filter assembly suitable for use in an implantable medical device or the like, wherein the feedthrough assembly includes a laminar delamination gap for accommodating and facilitating post-manufactured hermetic seal testing.

SUMMARY OF THE INVENTION

In accordance with the invention, an improved electromagnetic interference (EMI) feedthrough filter assembly for use in an active implantable medical device (AIMD) is provided. The assembly comprises a capacitor having first and second sets of electrode plates embedded within a dielectric body such as a monolithic ceramic material. A conductive ferrule is conductively coupled to the second set of electrode plates. An insulator is adjacent to an axial side of the capacitor and extends across and seals an aperture in the ferrule. A conductive terminal pin extends through the capacitor and insulator in conductive relation with the first set of electrode plates. A washer is disposed between the insulator and the capacitor body, wherein the insulator and the washer cooperatively define a laminator delamination gap.

The assembly may further comprise an adhesive layer disposed between the capacitor and the washer that laminates the washer to the capacitor following a curing process. The adhesive layer may be formed from a liquid polymer, an adhesive washer, a thermo plastic adhesive coated material, or any similarly adhesive material. The washer may be formed from a non-conductive or insulative material, i.e., polyimide sheet or a thin sheet of alumina.

The assembly may include a plurality of terminal pins extending through the insulator and capacitor body in conductive relation with the first set of electrode plates. In addition, the insulator may comprise a plurality of insulators corresponding to a plurality of ferrule apertures.

The assembly is designed to be used with various AIMDs, including but not limited to, cardiac pacemakers, cardiac sensing systems, neurostimulators, cochlear implants, deep brain stimulators, implantable defibrillators, congestive heart failure devices, hearing implants, drug pumps, ventricular assist devices, insulin pumps, spinal cord stimulators, artificial hearts, incontinence devices, bone growth stimulators, gastric pacemakers, or prosthetic devices.

Additional objects and advantages of the invention will be set forth in part in the drawings which follow, and in part will be obvious from the description or may be learned by practice of the invention. It is to be understood that both the foregoing general description and the following drawings are exemplary and explanatory only and are not restrictive of the invention as to be claimed.

BRIEF DESCRIPTION OF THE DRAWINGS

The accompanying drawings illustrate the invention. In such drawings.

DETAILED DESCRIPTION OF THE PREFERRED EMBODIMENTS

An improved feedthrough capacitor filter assembly is provided for use in active implantable medical devices (AIMDs) and the like, such as in a cardiac pacemaker, a cardiac sensing system, a neurostimulator, a cochlear implant, a deep brain stimulator, an implantable defibrillator, a congestive heart failure device, a hearing implant, a drug pump, a ventricular assist device, an insulin pump, a spinal cord stimulator, an artificial heart, an incontinence device, a bone growth stimulator, a gastric pacemaker, or a prosthetic device. This improved filter assembly includes a laminar delamination gap for facilitated hermetic seal testing subsequent to manufacture and prior to use.

Figure 1:
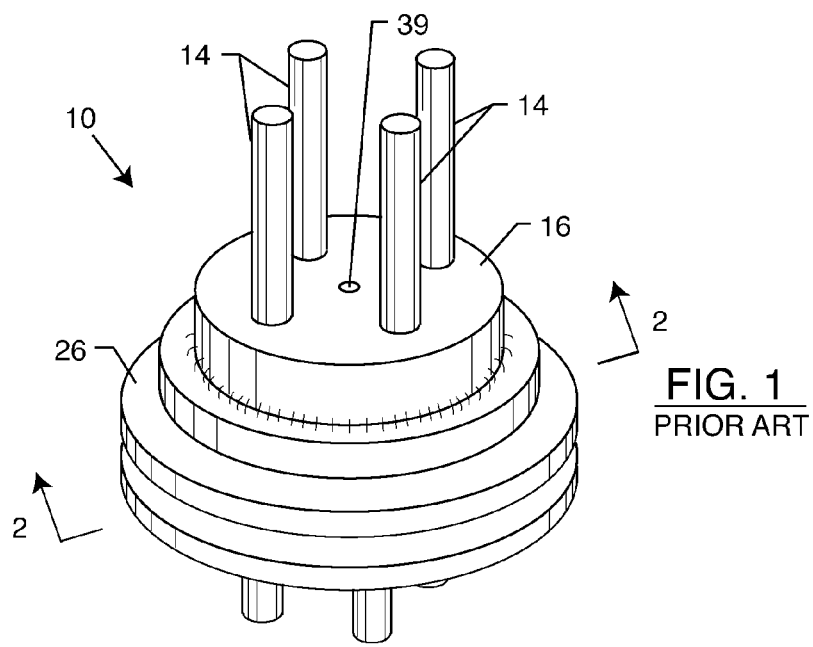
FIG. 1 is an isometric view of a prior art quadpolar feedthrough capacitor mounted to a quadpolar hermetic terminal.
Figure 2:
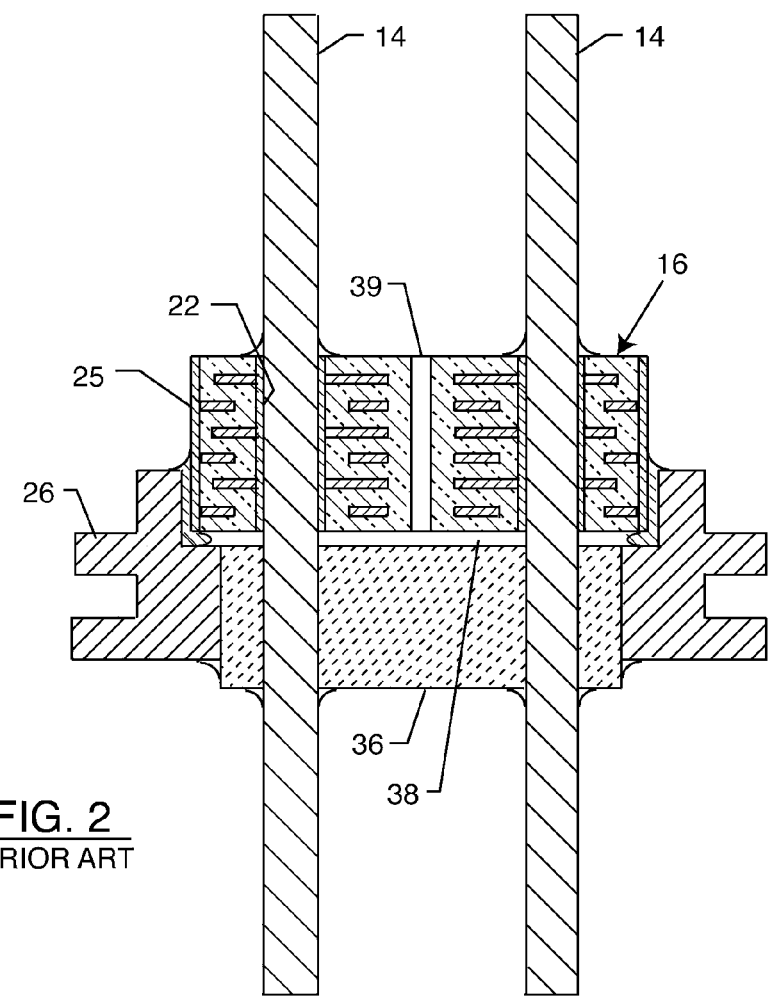
FIG. 2 is a cross-sectional view taken along line 2-2 of FIG. 1.

FIGS. 1 and 2, taken from FIGS. 1 and 2 of U.S. Pat. No. 6,566,978, depict a variation on a feedthrough filter assembly 10 with a leak detection vent 39 from the prior art. In this prior art form, the feedthrough filter assembly 10 comprises a capacitor body 16, at least one terminal pin 14 extending through the capacitor 16, an outer ferrule 26 mounted about the capacitor 16, an insulator 36 seated within or over the ferrule 26 at one side of the capacitor 16 providing an hermetic seal, and a leak detection vent 38, 39 formed in the assembly 10. The leak detection vent 38, 39 is designed to accommodate and facilitate post-assembly fluid leak testing of the hermetic seal, by subjecting the hermetic seal to a selected pressurized test gas such as helium or the like, prior to implantation of the assembly 10 in a medical device into a patient. In the described embodiments, the insulator 36 and capacitor 16 are separated by a short axial gap 38 created by the presence of a dissolvable washer. This gap provides access to a leak detection vent or passage 39, which facilitates detecting the presence of the test gas leaking past the hermetic seal.

Figure 3:
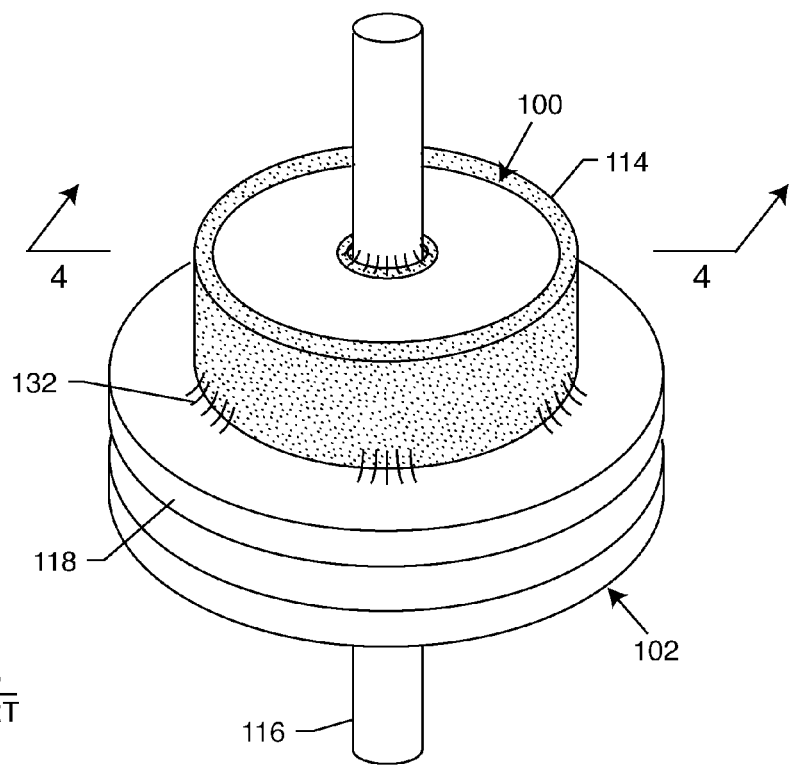
FIG. 3 is an isometric view of a prior art unipolar feedthrough capacitor mounted to a unipolar hermetic terminal.
Figure 4:
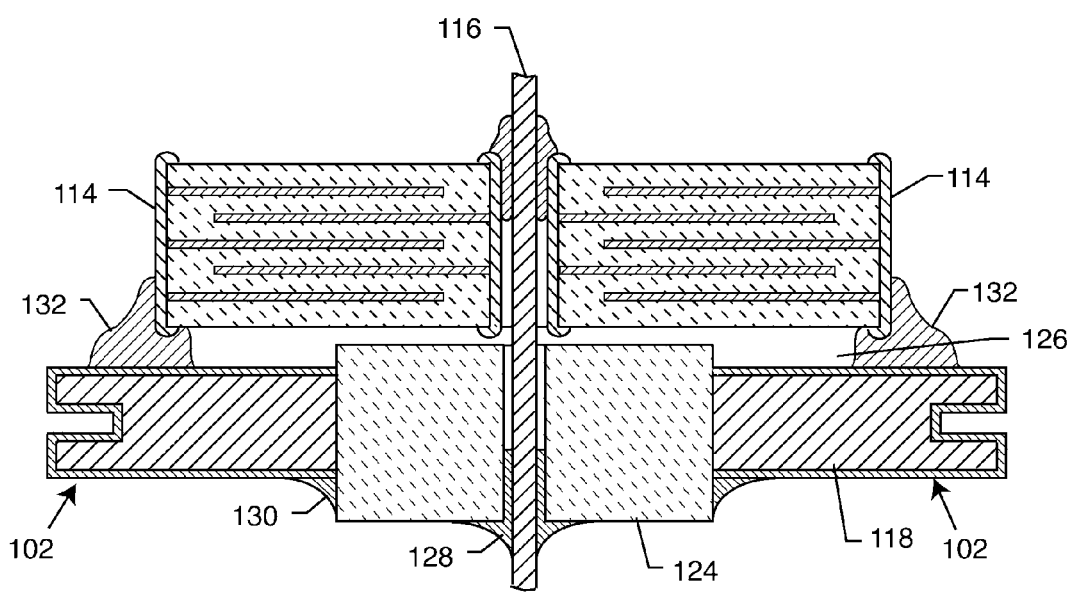
FIG. 4 is a cross-sectional view taken along line 4-4 of FIG. 3.
Figure 5:
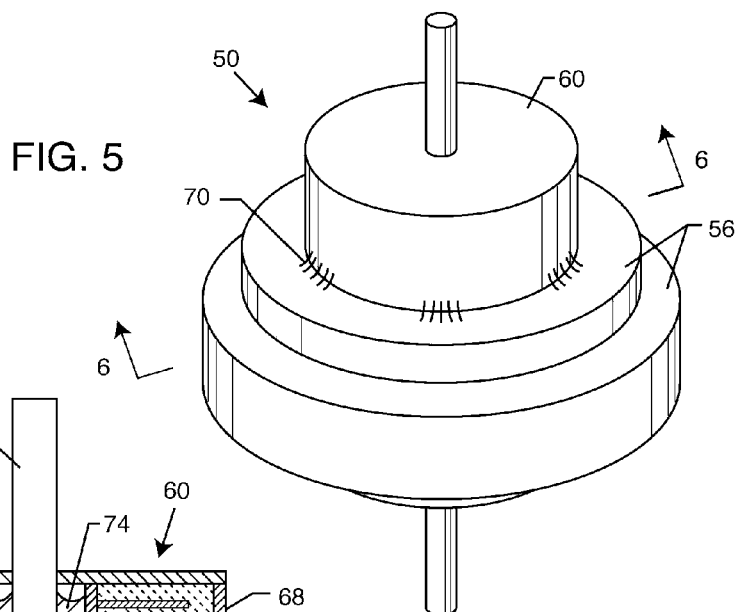
FIG. 5 is an isometric view of a unipolar feedthrough capacitor mounted to a unipolar hermetic terminal embodying the present invention.
Figure 6:
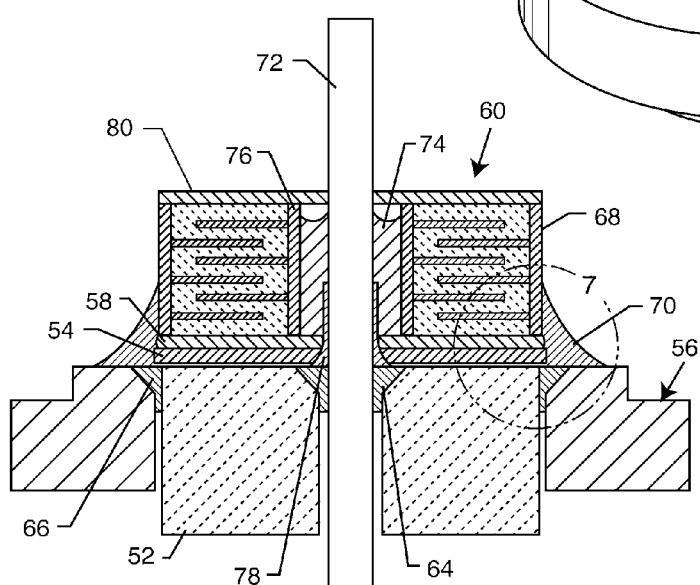
FIG. 6 is a cross-sectional view taken along line 6-6 of FIG. 5.

Similarly, FIGS. 3 and 4, taken from FIGS. 5 and 6 of U.S. Pat. No. 6,765,779, depict other prior art embodiments of capacitors 100 mounted on terminals 102 employing alternate configurations for leak detection. The terminal 102 comprises a capacitor 100, a ferrule 118 having a central aperture, an insulator 124 within the central aperture to prevent passage of fluid such as patient body fluids, and a terminal pin 116. The insulator 124 and the capacitor 100 cooperate to define a short axial gap 126 therebetween. This gap 126 forms a leak detection vent and facilitates leak detection. The capacitor 100 is mechanically and conductively attached to the ferrule 118 by means of peripheral support material 132 while maintaining the axial gap 126 between the capacitor 100 and the insulator 124. The axial gap 126 is small to preclude leakage of EMI. The peripheral support material 132 is preferably to allow for passage of helium during hermetic seal testing of the complete assembly. As shown in FIG. 2, there are substantial gaps between instances of the peripheral support material 132, which allows for the passage of helium during a leak detection test.

The teachings as described in U.S. Pat. Nos. 6,566,978 and 6,765,779 are incorporated by reference herein in their entirety. As discussed above, there are various drawbacks associated with each of the devices taught by these prior art devices and the associated methods of leak detection.

In the present invention, FIGS. 5 and 6 illustrate a unipolar device 50 similar to that previously described in U.S. Pat. No. 6,765,779. However, there are a number of important improvements. The alumina ceramic insulator 52 has been modified so that it is flush with the ferrule 56 and does not extend upward, above the top surface of the ferrule 56. A non-conductive and non-adhesive washer 54 has been added and is pressed firmly against the top surface of the alumina insulator 52. (This could also be pressed against the top surface of the ferrule 56.) This non-adhesive washer 54 is typically formed from a high temperature material such as a non-conductive polyimide sheet. This is convenient in that the washer 54 material can be shaped by die cutting, laser cutting or the like. The non-adhesive washer 54 can also be formed of a thin sheet of alumina or other suitable insulating material. The important feature is that the non-adhesive washer 54 be flat and have the ability to be pressed firmly down against the alumina or equivalent insulator 54. One or more adhesive layers 58, i.e., liquid polymer washers, are then placed on top of the washer 54. The most suitable material for this is a thermal plastic adhesive coated tape material. The capacitor 60 is then seated into place. Conformal coating 80 is optional and can be deposited on the top surface of the capacitor to improve its high voltage standoff capability and/or its moisture resistance.

The entire assembly is pre-weighted and then cured at an elevated temperature. Since both the top and bottom surfaces of the adhesive layer 58 are coated with an adhesive, they laminate both to the bottom of the ceramic capacitor 60 and to the top of the non-adhesive washer 54. It is an important feature of the present invention that the bottom surface of the non-adhesive washer 54 not be laminated to the top surface of the insulator 52 or the ferrule 56 of the terminal 50. This leaves a very thin laminar delamination gap 62 which is best seen in the exploded view of FIG. 7. Even in FIG. 7, delamination gap 62 is exaggerated in thickness for purposes of depiction. In application, delamination gap 62 is a very thin gap on the order of 50 angstroms or so. However, this small delamination gap 62 is sufficient to readily allow helium atoms to pass during a helium leak detection test. For example, if either or both braze joint 64 or 66 were defective, this would allow helium to penetrate through the defective braze 64 or 66 or a corresponding crack in the alumina insulator 52 into the laminar delamination gap 62 and out to the other side of ferrule 56 where it could be readily detected by the helium leak detector.

It is useful to look at the size of the elements that are involved. For example, the atomic radius of a helium atom is 0.49 angstroms. The diameter therefore is 0.98 angstroms. The diameter of a nitrogen atom is 1.5 angstroms. A nitrogen molecule is composed of two nitrogen atoms bonded to each other. The molecule has an elliptical shape. However, helium atoms do not bond to each other. Thus, the "molecule" is represented by a single helium atom. Thus, we can compare a sphere of 0.98 angstroms in diameter for the helium atom to an oval shape whose longest length is about 3 angstroms for the nitrogen molecule. A complicating factor is that atoms and molecules are not "hard spheres" so that the size of molecules and atoms depends somewhat on how you make the measurement. The inter-atomic distance for nitrogen ($N_2$) obtained from an electronic spectrum is 109.7 nanometers compared to 298 nanometers for diatomic ($He_2$) obtained from quantum mechanical calculations. Quantum mechanical calculations of the orbital radius of He and N atoms are 291 and 521 nanometers respectively. Commonly used molecular models for water utilize O—H lengths between 0.957 angstrom and 1.00 angstrom and H—O—H angles of 104.52 degrees to 109.5 degrees. The van der Waals diameter of water has been reported as identical with that of isoelectronic neon (2.82 angstroms). Molecular model values and intermediate peak radial distribution data indicates however that it is somewhat greater (3.2 angstroms). Another important feature of water is its polar nature. The water molecule forms an angle with hydrogen atoms at the tips and oxygen at the vertex. Since oxygen has higher electrodenegativity than hydrogen, the side of the molecule with the oxygen molecule has a partial negative charge. A molecule with such a charge difference is called a dipole. The charge differences cause water molecules to be attracted to each other and to other polar molecules. This is known as hydrogen bonding. These are some of the properties that cause water to form a liquid at room temperature and to also have relatively high surface tension. The strong hydrogen bonds give water a high cohesiveness and consequently high surface tension. This is evident when small quantities of water are put onto a non-soluble surface and the water stays together as drops. Accordingly, when comparing the ability of a single helium atom to penetrate into a delamination gap as compared to water, one needs to compare more than just the atomic radii. Experts in leak detection generally consider that a helium atom will penetrate into a small delamination gap or separation between 100 to 500 times more readily than water.

A significant advantage of this is that the large gap as previously described above in the prior art and shown in FIGS. 1 through 4 has been eliminated. By providing a thin and controllable delamination gap 62, water has been generally precluded from entering the space between the non-adhesive washer 54 and the insulator 52; however, helium is free to flow. This is also very important during water cleaning after sodium bicarbonate blasting. Accordingly, since water molecules do not readily penetrate the laminar delamination gap 62, this also means that the ionically dissolved sodium bicarbonate, which is contained in the water, will not deposit in this surface area.

Figure 7:
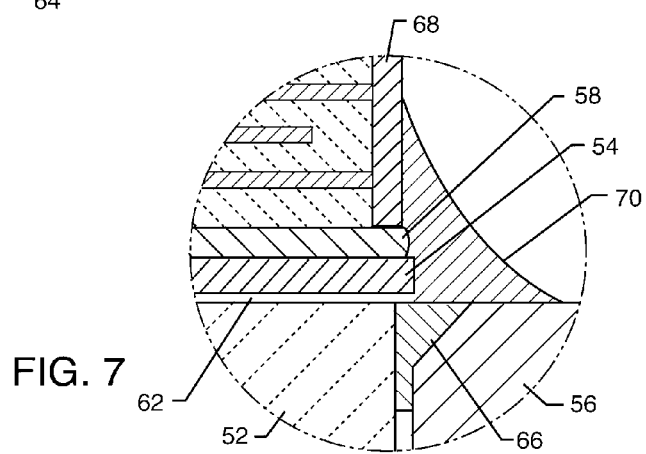
FIG. 7 is a fragmented exploded view taken of the area indicated by the number 7 in FIG. 6.

It is an important property of electro-physics that the smaller you make an air gap or separation, the higher the voltage breakdown strength becomes. The breakdown strength of air increases dramatically in very small separation spaces. Accordingly, the dielectric field breakdown strength of a delamination gap 62 such as shown in FIGS. 6 and 7 is extraordinarily high (on the order of 300 volts per mil or even higher). In a larger gap, air can break down at 60 to 90 volts per mil. Referring now again to FIGS. 5 and 6, the connection 70 between the capacitor 60 outside diameter termination 68 and the ferrule 56 is shown. Connection 70 is typically a conductive thermal setting polyimide or the like. As described in U.S. Pat. No. 6,566,978 and other patents, it is desirable that this electrical connection material 70 be discontinuous around the outside diameter of ceramic capacitor 60. This demonstrates the fact that any helium that is contained within the laminar delamination gap 62 can pass readily to the outside of the ceramic capacitor 60.

There is the ability to use lead wires 72 that tend to have non-conductive surfaces due to corrosion or oxides, described in U.S. Pat. No. 6,566,978 and incorporated by reference herein in its entirety. This includes the family of niobium and tantalum. It is desirable to have the inside diameter electrical connection 74 make direct contact to gold braze joint 64. In this regard, it is necessary to form a low impedance electrical connection between the capacitor inside diameter termination 76 directly to lead wire 72. In this case, the electrical connection 74 is from the inside diameter termination 76 through the conductive thermal setting polymer 74 directly to gold braze joint 64 and then in turn to lead wire 72. It should be noted that gold braze joint 64 is formed at an elevated temperature sufficient to burn through any surface contamination, oxide or corrosion product on the surface of lead wire 72. Accordingly, the connection between the gold braze joint 64 and the lead wire 72 is metallurgic and very low impedance. However, in accordance with an embodiment of the present invention, the inside diameter termination 76 of the feedthrough capacitor 60 has been sealed off from the gold braze joint 64 by means of washer 54 and adhesive layer 58 as shown. That is, electrical connection 74 is not free to penetrate down and touch off against the gold braze joint 64. It is in another embodiment of the present invention that prior to placement of washer 54, and adhesive layer 58 and capacitor 60, that conductive thermal setting or solder material 78 be placed from the gold braze joint 64 partially up the lead wire 72. This forms a low resistance and low impedance electrical connection that is continuous from the gold braze joint 64 up along the sides of the lead wire 72 to a datum that is above the level of adhesive layer 58. Accordingly, after the washer 54, adhesive layer 58 and capacitor 60 are placed and cured together, it is then possible to subsequently add electrical connection material 74 such that it forms a low impedance electrical connection between the electrical connecting material 78 and the inside diameter of the feedthrough capacitor 76.

The geometries and shapes of the unipolar assemblies, as illustrated in FIGS. 5-7, can be extended to a variety of geometries and shapes including quadpolar, dual inline octapolar, inline nine polar and the like. In other words, this laminar delamination principle as described herein, can literally be applied to any feedthrough capacitor assembly for human implant.

Figure 8:
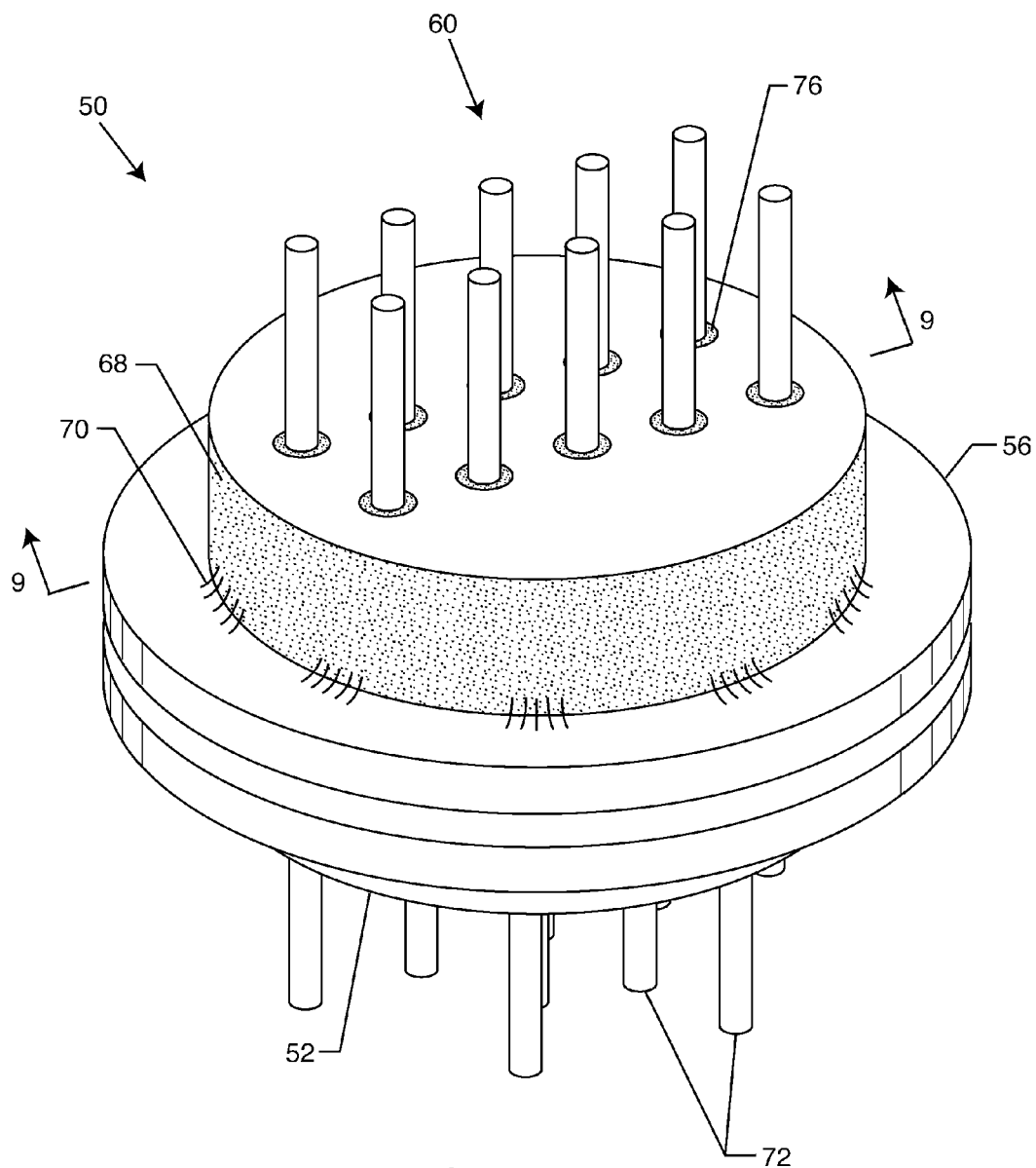
FIG. 8 is an isometric view of another embodiment of the present invention.
Figure 9:
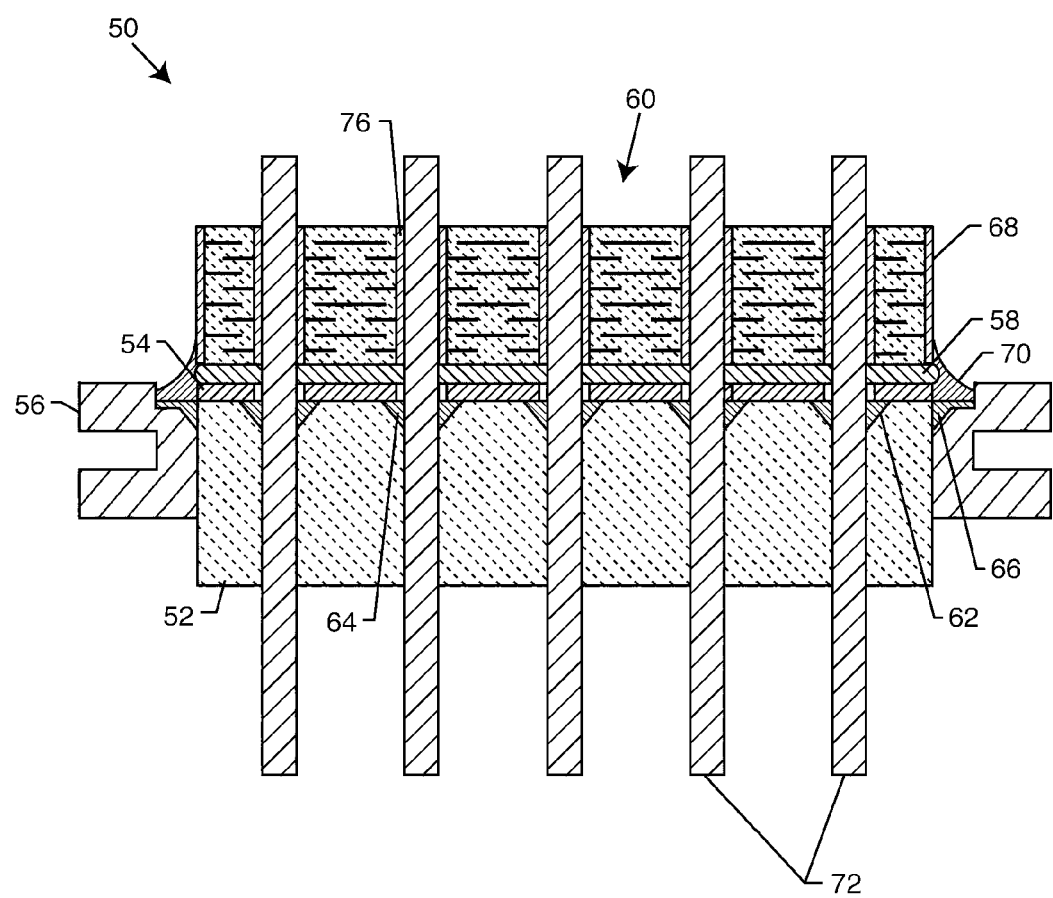
FIG. 9 is a cross-sectional view taken along line 9-9 of FIG. 8.

For example, FIGS. 8 and 9 illustrate an alternate embodiment of the present invention in view of the above. In this case, the lead wires 72 are of platinum or of platinum iridium construction, which is a suitable biocompatible material. Platinum or platinum iridium does not form heavy oxides. Accordingly, one can make a low impedance electrical connection directly from the capacitor inside diameter termination 76 to the lead wire 72 itself. This eliminates the need for the application of the material 78 as previously described in FIG. 6. In accordance with the present invention, non-adhesive washer 54 has been placed against the top surface of the alumina insulator 52. Then an adhesive layer 58, i.e., liquid thermal setting conductive polymer washer, is placed such that it will bond to the top surface of the non-adhesive washer 54. The ceramic capacitor 60 is then placed in sandwich construction over the other surface of the adhesive layer 58. Depending upon the dimensions required, the adhesive layer 58 can be formed as a single unit or several adhesively coated units stacked together. The assembly is then compressed with a weighting fixture and cured at elevated temperature. As in the alternate embodiment, because the bottom surface of the non-adhesive washer 54 is pressed against the top surface of the alumina or glass hermetic insulator 52, a very small space is formed as a laminar delamination gap between the two surfaces. This laminar delamination gap 62 occurs since there are no adhesive materials in this space. As previously discussed in accordance with an embodiment of the present invention, this laminar delamination gap 62 is sufficient to allow for ready passage of helium molecules during a helium leak test. Accordingly, if there was a micro fracture within the hermetic insulator 52 or a defective gold braze joint 64 or 66, then helium molecules could readily pass through the laminar delamination gap 62 of the present invention and then flow out to be detected by the helium leak detection equipment. As previously described, the electrical connection material 70 that connects the capacitor outside diameter 68 to the gold braze 66 of ferrule 56 is discontinuous. That is, it does not go around the entire perimeter or outside diameter of the feedthrough capacitor 60. These gaps are important so that helium flowing through the laminar delamination gap 62 is not blocked by the connection material 70 and can flow readily outside of the ceramic capacitor 60.

Referring now back to FIG. 8, there are a number of possible alternatives available. One alternative would be a simple inline, which would make for a five pin 72 feedthrough. Another alternative could be of a dual inline configuration making for a total of ten feedthrough pins 72. In accordance with an embodiment of the present invention, one or more of these pins 72 could be grounded and the capacitor 60 could even be of internally grounded construction. Another possible alternative for the ceramic capacitor assembly 50 described in FIG. 8 would be circular or oval shape when viewed from above. In this case, there could be many more pins.

Although several embodiments of the invention have been described in detail for purposes of illustration, various modifications of each may be made without departing from the spirit and scope of the invention. Accordingly, the invention is not limited, except by the appended claims.

What is claimed is:

1. An EMI feedthrough filter assembly for use in an active implantable medical device (AIMD), comprising:
    a capacitor having first and second sets electrode plates;
    a conductive ferrule conductively coupled to the second set of electrode plates;
    an insulator at one axial side of capacitor, extending across and sealing an aperture in the ferrule;
    a conductive terminal pin extending through the insulator and the capacitor in conductive relation with the first set of electrode plates;
    a washer disposed between the insulator and the capacitor, wherein the insulator and the washer cooperatively define a laminar delamination gap; and
    an adhesive layer disposed between the capacitor and the washer.

2. The EMI feedthrough filter assembly of claim 1, wherein the adhesive layer is formed from a liquid polymer, an adhesive washer, or a thermal plastic adhesive coated material.

3. The EMI feedthrough filter assembly of claim 1, wherein the conductive terminal pin comprises a corresponding plurality of conductive terminal pins extending respectively through the insulator and the capacitor in conductive relation with the first set of electrode plates.

4. The EMI feedthrough filter assembly of claim 3, wherein the insulator comprises a plurality of insulators corresponding to a plurality of ferrule apertures.

5. The EMI feedthrough filter assembly of claim 1, wherein the washer is formed from a nonconductive polyimide sheet or a thin sheet of alumina.

6. The EMI feedthrough filter assembly of claim 1, wherein the AIMD is a cardiac pacemaker, a cardiac sensing system, a neurostimulator, a cochlear implant, a deep brain stimulator, an implantable defibrillator, a congestive heart failure device, a hearing implant, a drug pump, a ventricular assist device, an insulin pump, a spinal cord stimulator, an artificial heart, an incontinence device, a bone growth stimulator, a gastric pacemaker, or a prosthetic device.

7. An EMI feedthrough filter assembly for use in an active implantable medical device (AIMD), comprising:
    a capacitor having first and second sets electrode plates, the second set of electrode plates being grounded to the AIMD;
    an insulator at one axial side of capacitor;
    a conductive terminal pin extending through the insulator and the capacitor in conductive relation with the first set of electrode plates;
    a washer disposed between the insulator and the capacitor, wherein the insulator and the washer cooperatively define a laminar delamination gap; and
    an adhesive layer between the capacitor and the washer, the adhesive layer formed from a liquid polymer, an adhesive washer, or a thermal plastic adhesive coated material.

8. The EMI feedthrough filter assembly of claim 7, wherein the conductive terminal pin comprises a corresponding plurality of conductive terminal pins extending respectively through the insulator and the capacitor in conductive relation with the first set of electrode plates.

9. The EMI feedthrough filter assembly of claim 8, wherein the insulator comprises a plurality of insulators corresponding to a plurality of ferrule apertures.

10. The EMI feedthrough filter assembly of claim 7, wherein the washer is formed from a non-conductive polyimide sheet or a thin sheet of alumina.

11. The EMI feedthrough filter assembly of claim 7, wherein the AIMD is a cardiac pacemaker, a cardiac sensing system, a neurostimulator, a cochlear implant, a deep brain stimulator, an implantable defibrillator, a congestive heart failure device, a hearing implant, a drug pump, a ventricular assist device, an insulin pump, a spinal cord stimulator, an artificial heart, an incontinence device, a bone growth stimulator, a gastric pacemaker, or a prosthetic device.

12. An EMI feedthrough filter assembly for use in an active implantable medical device (AIMD), comprising:
    a capacitor having first and second sets electrode plates, the second set of electrode plates being grounded to the (AIMD);
    an insulator at one axial side of capacitor;
    a conductive terminal pin extending through the insulator and the capacitor in conductive relation with the first set of electrode plates; and
    a washer disposed between the insulator and the capacitor, wherein the insulator and the washer cooperatively define an adhesive layer, a laminar delamination gap, disposed between the capacitor and the washer, such that the capacitor, adhesive layer and washer are laminated together.

13. The EMI feedthrough filter assembly of claim 12, wherein the conductive terminal pin comprises a corresponding plurality of conductive terminal pins extending respectively through the insulator and the capacitor in conductive relation with the first set of electrode plates.

14. The EMI feedthrough filter assembly of claim 13, wherein the insulator comprises a plurality of insulators corresponding to a plurality of ferrule apertures.

15. The EMI feedthrough filter assembly of claim 12, wherein the AIMD is a cardiac pacemaker, a cardiac sensing system, a neurostimulator, a cochlear implant, a deep brain stimulator, an implantable defibrillator, a congestive heart failure device, a hearing implant, a drug pump, a ventricular assist device, an insulin pump, a spinal cord stimulator, an artificial heart, an incontinence device, a bone growth stimulator, a gastric pacemaker, or a prosthetic device.

16. An EMI feedthrough filter assembly for use in an electronic device (AIMD), comprising;
    a capacitor having first and second sets electrode plates;
    a conductive ferrule conductively coupled to the second set of electrode plates;
    an insulator at one axial side of capacitor, extending across and sealing an aperture in the ferrule;

a conductive terminal pin extending through the insulator and the capacitor in conductive relation with the first set of electrode plates;

a washer disposed between the insulator and the capacitor, wherein the insulator and the washer cooperatively define a laminar delamination gap; and an adhesive layer disposed between the capacitor and the washer.

17. The EMI feedthrough filter assembly of claim 16, wherein the adhesive layer is formed from a liquid polymer, an adhesive washer, or a thermal plastic adhesive coated material.

18. The EMI feedthrough filter assembly of claim 16, wherein the conductive terminal pin comprises a corresponding plurality of conductive terminal pins extending respectively through the insulator and the capacitor in conductive relation with the first set of electrode plates.

19. The EMI feedthrough filter assembly of claim 18, wherein the insulator comprises a plurality of insulators corresponding to a plurality of ferrule apertures.

20. The EMI feedthrough filter assembly of claim 16, wherein the washer is formed from a nonconductive polyimide sheet or a thin sheet of alumina.

* * * * *